(12) United States Patent
Jaramaz et al.

(10) Patent No.: US 11,992,269 B2
(45) Date of Patent: *May 28, 2024

(54) SYSTEMS AND METHODS FOR PLANNING AND PERFORMING IMAGE FREE IMPLANT REVISION SURGERY

(71) Applicant: Blue Belt Technologies, Inc., Memphis, TN (US)

(72) Inventors: Branislav Jaramaz, Pittsburgh, PA (US); Alberto Gregori, Hamilton (GB)

(73) Assignee: Blue Belt Technologies, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,123

(22) Filed: Dec. 23, 2022

(65) Prior Publication Data
US 2023/0131309 A1    Apr. 27, 2023

Related U.S. Application Data

(63) Continuation of application No. 16/545,431, filed on Aug. 20, 2019, now Pat. No. 11,559,356, which is a
(Continued)

(51) Int. Cl.
*A61B 34/10* (2016.01)
*A61B 5/06* (2006.01)
(Continued)

(52) U.S. Cl.
CPC .............. *A61B 34/10* (2016.02); *A61B 5/065* (2013.01); *A61B 34/20* (2016.02); *A61B 34/30* (2016.02); *A61B 34/35* (2016.02); *G06T 17/10* (2013.01); *G06T 19/20* (2013.01); *G16H 50/50* (2018.01); *A61B 2034/105* (2016.02);
(Continued)

(58) Field of Classification Search
CPC ......... A61B 34/10; A61B 5/065; A61B 34/20; A61B 34/30; A61B 34/35; A61B 2034/105; A61B 2034/107; A61B 2034/108; A61B 2034/2055; A61B 2034/2063; A61B 2034/2068; G06T 17/10; G06T 19/20; G06T 2210/41; G06T 2219/2021; G16H 50/50

See application file for complete search history.

(56) References Cited

U.S. PATENT DOCUMENTS 6,757,582 B2 * 6/2004 Brisson ................. A61B 90/10
                                                         83/768
7,715,602 B2 * 5/2010 Richard ................. A61B 90/36
                                                         606/88

(Continued)

*Primary Examiner* — Sanjay Cattungal
(74) *Attorney, Agent, or Firm* — DLA Piper LLP

(57) ABSTRACT

Systems and methods for planning and performing image free implant revision surgery are discussed. For example, a method for generating a revision plan can include collecting pre-defined parameters characterizing a target bone, generating a 3D model, collecting a plurality of surface points, and generating a reshaped 3D model. Generating the 3D model of the target bone can be based on a first portion of the pre-defined parameters. Generating the reshaped 3D model can be done based on the plurality of surface points collected from a portion of the surface of the target bone.

17 Claims, 7 Drawing Sheets

Related U.S. Application Data continuation of application No. 14/955,742, filed on Dec. 1, 2015, now Pat. No. 10,537,388.

(60) Provisional application No. 62/085,647, filed on Dec. 1, 2014.

(51) Int. Cl.
*A61B 34/20* (2016.01)
*A61B 34/30* (2016.01)
*A61B 34/35* (2016.01)
*G06T 17/10* (2006.01)
*G06T 19/20* (2011.01)
*G16H 50/50* (2018.01)

(52) U.S. Cl.
CPC ... *A61B 2034/107* (2016.02); *A61B 2034/108* (2016.02); *A61B 2034/2055* (2016.02); *A61B 2034/2063* (2016.02); *A61B 2034/2068* (2016.02); *G06T 2210/41* (2013.01); *G06T 2219/2021* (2013.01)

(56) References Cited

U.S. PATENT DOCUMENTS

| | | | | |
|---|---|---|---|---|
| 8,165,659 | B2* | 4/2012 | Sheffer | A61B 34/20 600/407 |
| 9,724,165 | B2* | 8/2017 | Arata | A61B 34/20 |
| 2008/0004633 | A1* | 1/2008 | Arata | A61B 34/71 606/130 |
| 2008/0119724 | A1* | 5/2008 | Williamson | A61B 5/06 600/424 |
| 2014/0208578 | A1* | 7/2014 | Linderman | A61B 17/1746 623/18.11 |

\* cited by examiner

SYSTEMS AND METHODS FOR PLANNING AND PERFORMING IMAGE FREE IMPLANT REVISION SURGERY

CLAIM OF PRIORITY

This application is a continuation of U.S. patent application Ser. No. 16/545,431, filed Aug. 20, 2019 and titled "Systems and Methods for Planning and Performing Image Free Implant Revision Surgery," which is a continuation of U.S. patent application Ser. No. 14/955,742, filed Dec. 1, 2015 and titled "Systems and Methods for Planning and Performing Image Free Implant Revision Surgery," which claims the benefit of priority of U.S. Provisional Application No. 62/085,647, titled "Method for Planning and Performing CT-Less Implant Revision Surgery," filed on Dec. 1, 2014, each of which is hereby incorporated by reference herein in its entirety.

FIELD OF THE INVENTION

The present invention relates to the use of robotic systems in planning and performing orthopedic implant revision surgical procedures. One such type of robotic system, Precision Freehand Sculpting, (referred to herein as "PFS") is disclosed in more detail in U.S. Pat. No. 6,757,582, which is incorporated herein by reference in its entirety.

BACKGROUND

Implant revision surgery is performed to remove an orthopedic implant that has failed due to various causes, such as loosening, shifting, faulty alignment, wear, or other deterioration. Once the existing implant is removed and remaining bone surface is prepared, a new implant can be inserted. Implant revision surgery is commonly performed utilizing navigation methods to track the positions of the tools, bones, and implants involved. However, modern navigation methods still require numerous cutting guides, measurement jigs, and reassessment of bone resection surfaces, which results in unnecessarily time consuming procedures.

Problems with current revision techniques are compounded by the fact that removal of the existing implant in the revision procedure may result in additional damage to the bone surface, requiring further bone resection to prepare for insertion of the new implant. In some existing systems, additional imaging may also be required to develop a new surgical plan. Care must be taken to ensure implant fit in accordance with the patient's anatomy; however there is currently no method of performing implant revision surgical procedures employing methods that would simultaneously reduce the need for excess instrumentation and imaging, reduce the time required to perform the procedure, and ensure implant fit in accordance with the patient's anatomy. It is therefore an object of the present invention to provide a method of performing implant revision surgical procedures utilizing PFS, allowing a surgeon to plan bone refinement and implant placement on a virtual model of the patient's anatomy. The PFS system further allows the surgeon to precisely guide and execute the bone resection, resulting in efficiency in terms of instrumentation used and time spent. While the PFS system is discussed for purposes of example herein, those of skill in the art will recognize that other robotic surgical systems, such as Mako's Rio® system, can be used in conjunction with the methods of the present invention with only minor alterations that would be readily apparent to those of skill in the art.

In addition to the various objects and advantages of the present invention which have been described above, various other objects and advantages of the invention will become more readily apparent to those persons skilled in the relevant art from the following more detailed description of the invention, particularly, when such description is taken in conjunction with the attached drawing figures and with the appended claims.

BRIEF DESCRIPTION OF THE DRAWINGS

Some embodiments are illustrated by way of example and not limitation in the figures of the accompanying drawings in which.

OVERVIEW

Figure 1:
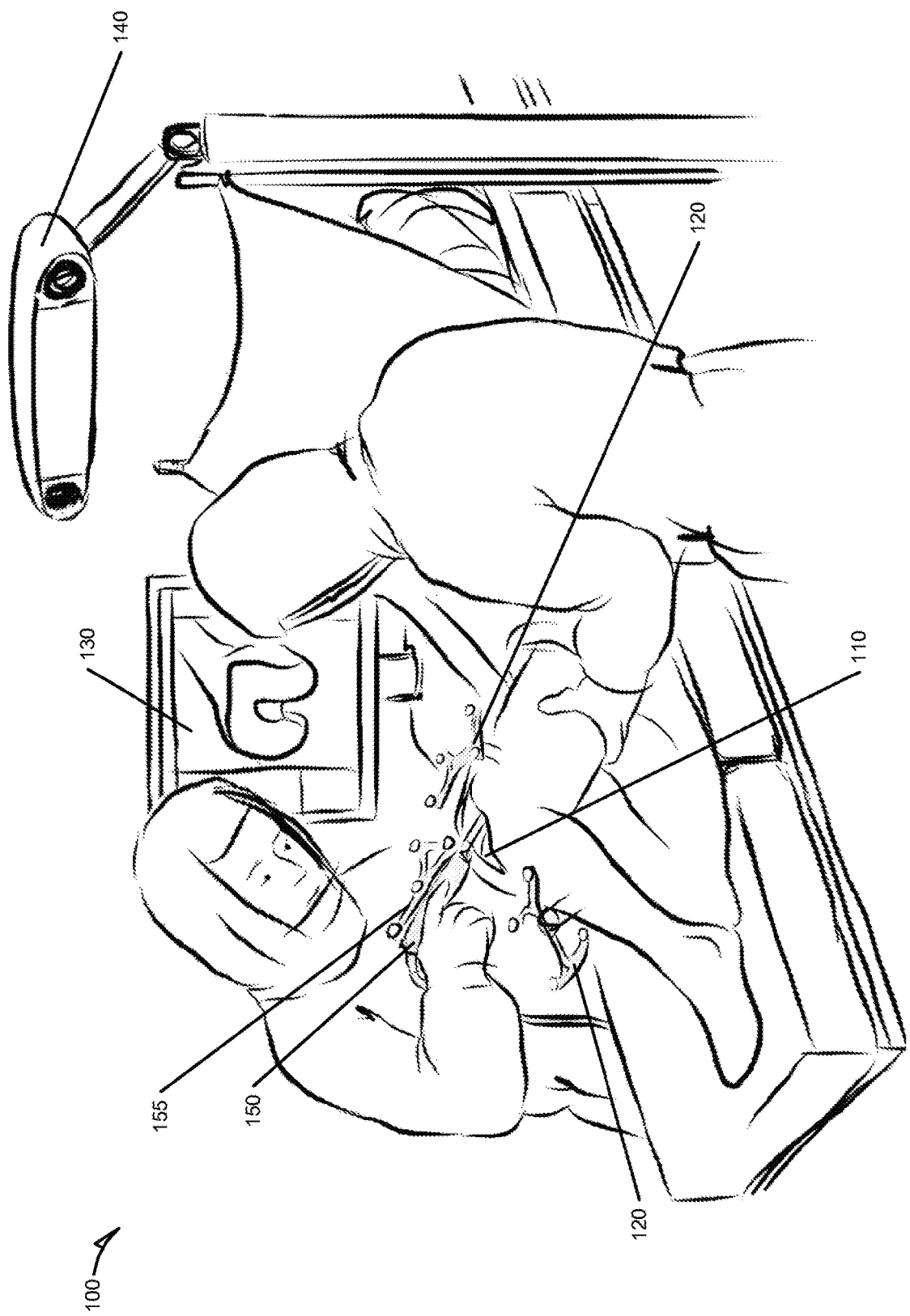
FIG. 1 is a diagram illustrating an environment for operating a system for planning and performing image free implant revision surgery, according to an example embodiment.

The present inventors have recognized, among other things, that current techniques used in orthopedic implant revision surgeries, such as revising a total knee replacement, fail to adequately account for specific shape and condition for the target bones, do not provide surgeons with methods to visualize implant and augment location, and do not provide patient specific outcomes that customize resections and implant locations.

Further, present systems to perform revision knee surgery require extensive instrumentation. This is required both for achieving alignment and position of selected implants. These instruments include alignment jigs, rods and multiple cutting blocks. The instruments mainly rely on generalized assumptions of anatomy, the systems and methods discussed herein allow for completely replacing these instruments with an individual intra-operatively derived, patient appropriate cutting plan.

Currently used instruments require fixation to the bones being operated upon, close to the implant interface. By the nature of the pathology requiring surgery, bone quality is often poor giving rise to inadequate or precarious fixation of cutting blocks and alignment jigs, this often causing unwanted movement of the jigs and resulting in inaccurate implant placement with subsequent deleterious effects on patient outcomes. The nature of the invention allows for this possibility to be overcome by placing trackers away from the operative field into better quality bone with more reliable fixation.

By removing the need for these instruments and their associated costs and burdens (sterilization, handling, transport, damage in transit etc.) the invention will in itself create a financial and logistical benefit to the user.

The following, non-limiting examples, detail certain aspects of the present systems and methods to solve the challenges and provide the benefits discussed herein.

Example 1 can include a method for creating a revision plan for use during an image free implant revision procedure. The method can include generating a 3D model, receiving a plurality of surface points, and generating a reshaped 3D model. The 3D model is generated to model the shape of at least a portion of the target bone associated with the implant revision procedure. The plurality of surface points are collected over a portion of the target bone surface associated with the implant revision procedure. The reshaped 3D model is generated based on the 3D model and the plurality of surface points collected from the portion of the target bone surface.

In Example 2, the method of Example 1 can optionally include generating a revision plan for preparing the target bone for implantation of prosthetic implants.

In Example 3, the methods of Example 2 can optionally include controlling a tracked surgical cutting instrument during resection of the target bone according to the revision plan.

In Example 4, the methods of any of Examples 1 to 3 can optionally include generating a voxelized 3D cylinder enclosing the portion of the target bone associated with the implant revision procedure. In some examples, the cylinder is larger in all dimensions as compared to the portion of the target bone associated with the implant revision procedure.

In Example 5, the methods of any of Examples 1 to 4 can optionally include generating the 3D model using a voxelized 3D model, and generating the reshaped 3D model by updating voxels within the voxelized 3D model based on the plurality of surface points.

In Example 6, the method of Example 5 can optionally include updating voxels within the voxelized 3D model includes performing volume subtraction from the 3D model based on the plurality of surface points.

In Example 7, the methods of any of Examples 1 to 6 can optionally include receiving a pre-defined set of parameters from a tracked surgical instrument characterizing the target bone; and wherein generating the 3D model includes calculating dimensions of the target bone from the pre-defined set of parameters.

In Example 8, the methods of any of Examples 1 to 7 can optionally include iteratively generating reshaped 3D model during collection of the plurality of surface points.

Example 9 can include a system for planning and performing image free implant revision surgery, including creating a revision plan. The system can include a surgical instrument, a tracking system, and a control system. The surgical instrument can include a tracking array. The tracking system can include a tracking sensor and can monitor, in real-time, three-dimensional position and orientation of the surgical instrument and at least one target bone of an implant host. The control system can include a communication interface and one or more processors coupled to a memory device. The communication interface can be coupled to the tracking system to receive tracking information identifying a current surgical instrument position and a current target bone position. The memory device can include instructions that, when executed by the one or more processors, cause the control system to perform operations including collecting pre-defined parameters, generating a 3D model, collecting a plurality of surface points, and generating a reshaped 3D model. The pre-defined parameters characterize a target bone in the implant revision procedure. The 3D model is generated from a portion of the pre-defined parameters to model the shape of at least a portion of the target bone. Optionally, a second portion of the pre-defined parameters is used to align the 3D model on the target bone within a working coordinate system. The plurality of surface points are collected over a portion of the target bone surface associated with the implant revision procedure. The reshaped 3D model is generated based on the 3D model and the plurality of surface points collected from the portion of the target bone surface.

In Example 10, the system of Example 9 can optionally include the surgical instrument with at least one of a cutting burr, a burr guard, a plate probe attachment, and a point probe.

In Example 11, the system of Example 10 can optionally include collecting the pre-defined parameters or the plurality of surface points using one of the cutting burr, the burr guard, the plate probe attachment, and the point probe.

In Example 12, the system of any of Examples 9 to 11 can optionally include the control system further performing operations including generating a revision plan for preparing the target bone for implantation of prosthetic implants.

In Example 13, the system of Example 12 can optionally include the communication interface coupled to the surgical instrument to send control signals to control a cutting burr. The control system can also perform operations including generating control signals to control the surgical instrument during resection of the target bone according to the revision plan, and communicating, over the communication interface, the generated controls signals to the surgical instrument.

In Example 14, the system of any of Examples 9 to 13 can optionally include generating the 3D model by generating a voxelized 3D cylinder enclosing the portion of the target bone associated with the implant revision procedure.

In Example 15, the system of Example 14 can optionally include generating the reshaped 3D model by performing volume subtraction from the 3D model based on the plurality of surface points.

In Example 16, the system of any of Examples 9 to 15 can optionally include generating the 3D model by accessing pre-operative medical imaging of the target bone to generate the 3D model.

In Example 17, the system of any of Examples 9 to 16 can optionally include iteratively generating reshaped model during collection of the plurality of surface points.

Example 18 can include a machine-readable storage medium with instructions that, when executed within a system for navigation and control of surgical instrument, perform the methods described in any one of Examples 1 to 9.

Example 19 can include a computer-implement method for planning an implant revision procedure. The method can include generating a 3D voxelized model, receiving a plurality of data points, calculating a set of waste voxels, and generating a reshaped 3D voxelized model. The 3D voxelized model can be generated to model a portion of a target bone associated with the implant revision procedure, wherein the model is at least as large, in every dimension, as the portion of the target bone. The plurality of data points are received from a tracking system tracking an instrument of known geometry as it is traced along a surface of the target bone. The set of waste voxels to be removed from the model are calculated based at least in part on the plurality of data points. The reshaped 3D voxelized model is generated based on the set of waste voxels.

Definitions

Implant—For the purposes of this specification and the associated claims, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

Implant host—For the purposes of this specification and the associated claims, the term "implant host" is used to refer to a patient. In certain instances the term implant host may also be used to refer, more specifically, to a particular joint or location of the intended implant within a particular patient's anatomy. For example, in a total hip replacement procedure the implant host may refer to the hip joint of the patient being replaced or repaired.

Real-time—For the purposes of this specification and the associated claims, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

DETAILED DESCRIPTION

Example systems and methods for planning and performing image free (CT-less) implant revision surgery are described. In some example embodiments, the systems and methods discussed herein can involve a combination of tracked point probe and computer-controlled surgical cutting instrument. In an example, the optically tracked point probe and computer-controlled surgical cutting instruments can be used to plan and execute a revision procedure to replace a defective orthopedic implant, such as a defective total knee replacement (TKA). In an example, a surgeon uses the point probe to map, in 3-dimensions, the actual surface of the target bone that needs a new implant. Mapping is performed after removal of the defective or worn-out implant, as well as after removal of any diseased or otherwise unwanted bone. The computer system can start the mapping process with a voxelized 3D model of the patient's bone aligned with landmark locations obtained using the tracked point probe or similar tracked surgical instrument. During the mapping process, using the tracked point probe, the cutting burr, burr guard, or plate probe attachment on the cutting instrument, the voxelized 3D model is reshaped based on actual surface data obtained from the patient's bone. Once the final 3D model is completed, the surgeon can move through the virtual 3D model layer by layer to assess revision implant location and fit. The detailed assessment allowed by the virtual 3D model produced using actual 3D surface data enables precise fit assessment (size and location), augment selection, and augment placement. Once the revision implants and any augments are located virtually within the 3D model environment, the system can generate a surgical cutting plan that will be implemented using the tracked and computer-controlled cutting instrument, such as PFS discussed above.

The method of conducting a revision procedure discussed herein enables a surgeon to more accurate place revision implants and augments, while avoiding the need for cutting guides and other complicated instrumentation. The practical effect of the discussed system within the operating room includes, fewer trays, less sterilization, and lower costs.

The following specification and associated figures describes example embodiments of the present invention with specific details. It will be evident, however, to one skilled in the art, that the present invention may be practiced without these specific details. It will also be evident that a computer controlled implant positioning system is not limited to the examples provided and may include other scenarios not specifically discussed.

FIG. 1 is an illustration of a system 100 for performing an image free (CT-less) revision surgical procedure using a robotic system. The system 100 includes a surgical cutting tool 150 with an associated optical tracking frame 155 (also referred to as tracking array 155), graphical user interface 130, an optical tracking system 140, and patient tracking frames 120 (also referred to as tracking arrays 120). The illustration also includes an incision 110, through which a knee revision surgery may be performed. In an example, the illustrated robotic surgical system 100 depicts a hand-held computer-controlled surgical robotic system, such as the Navio® Surgical System from Blue Belt Technologies of Plymouth, Minnesota. The illustrated robotic system uses an optical tracking system coupled to the robotic controller to track and control a hand-held surgical instrument. For example, the optical tracking system 140 tracks the tracking array 155 coupled to the surgical tool 150 and tracking arrays 120 coupled to the patient to track locations of the instrument relative to the target bone (e.g., femur and tibia for knee procedures).

Figure 2:
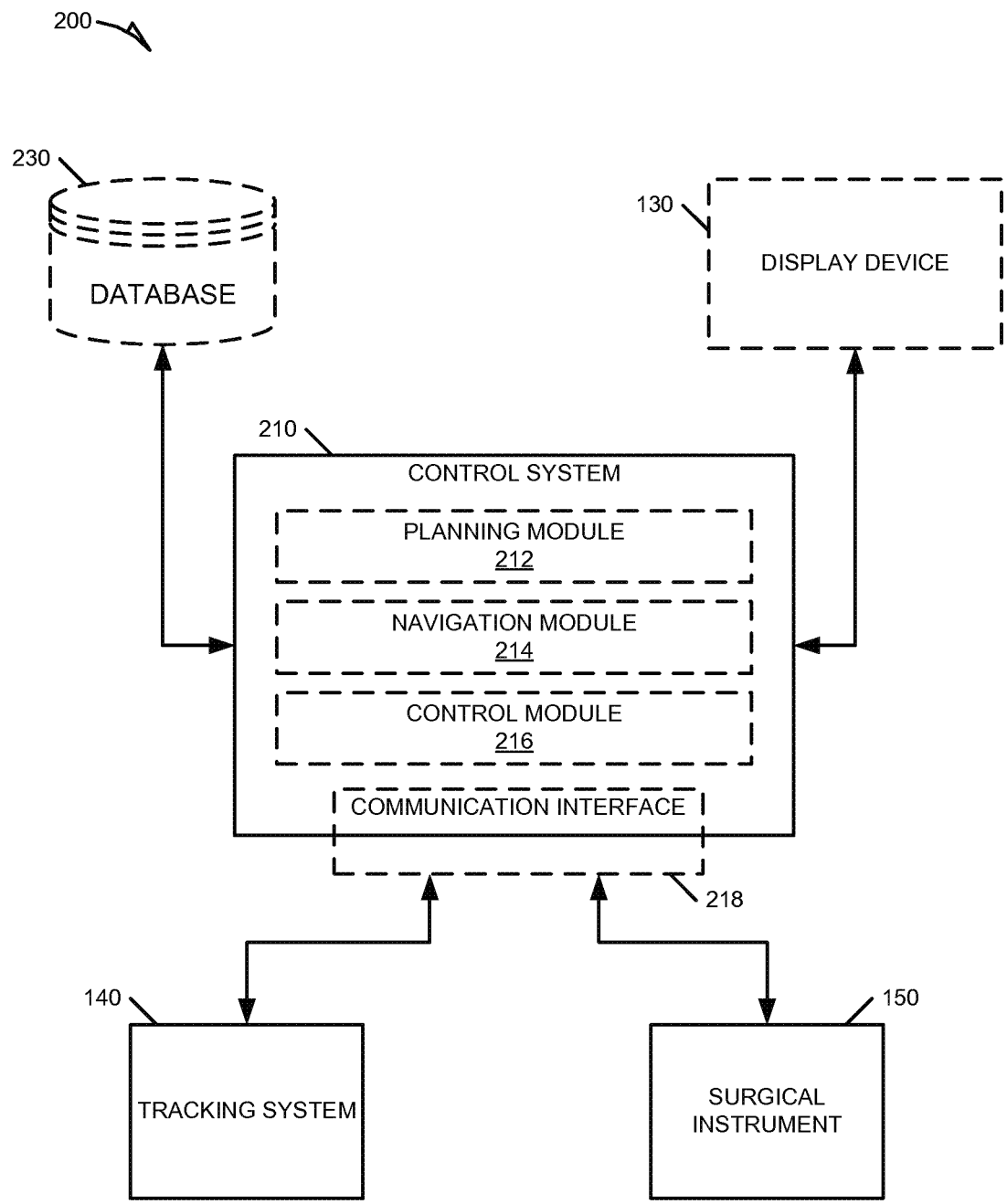
FIG. 2 is a block diagram depicting a system for planning and performing image free implant revision surgery, according to an example embodiment.

FIG. 2 is a block diagram depicting a system 200 for performing an image free (CT-less) revision surgical procedure, according to an example embodiment. In an example, the system 200 can include a control system 210, a tracking system 140, and a surgical instrument 150. Optionally, the system 200 can also include a display device 130 and a database 230. In an example, these components can be combined to provide navigation and control of the surgical instrument 150, which can include navigation and control of a cutting tool or a point probe, among other things, used during an orthopedic (or similar) prosthetic implant revision surgery.

The control system 210 can include one or more computing devices configured to coordinate information received from the tracking system 130 and provide control to the surgical instrument 150. In an example, the control system 210 can include a planning module 212, a navigation module 214, a control module 216, and a communication interface 218. In certain examples, the planning module 212 can provide pre-operative planning services that allow clinicians the ability to virtually plan a procedure prior to reshaping the target joint during the revision procedure on the patient. A portion of the planning process performed within the planning module can include operations similar to those discussed in U.S. Pat. No. 6,205,411 titled "Computer-assisted Surgery Planner and Intra-Operative Guidance System," to Digioia et al., which discusses yet another approach to pre-operative planning U.S. Pat. No. 6,205,411 is hereby incorporated by reference in its entirety.

In an example, such as a revision of a total knee arthroplasty (TKA), the planning module 212 can be used to manipulate a virtual model of the implant in reference to a virtual implant host model. As discussed in more detail below, the virtual model of the implant host (joint to be revised) can be created through use of a point probe or similar instrument tracked by the optical tracking system 140. The control system 210, in some examples the planning module 212, collects data from surfaces of the target joint to recreate a virtual model of the patient's actual anatomical structure. Particularly in a revision surgery, this method can increase the accuracy of the planning process by using data collected after the existing implants are removed and without intra-operative imaging. Collecting surface data from the target bone(s) can also allow for iterative reshaping of the target bone to ensure proper fit of new prosthetic implants and optimization of anatomical alignment.

In an example, the navigation module 214 can coordinate tracking the location and orientation of the implant, the implant host, and the surgical instrument 150. In certain examples, the navigation module 214 may also coordinate tracking of the virtual models used during pre-operative or intra-operative planning within the planning module 212. Tracking the virtual models can include operations such as alignment of the virtual models with the implant host through data obtained via the tracking system 140. In these examples, the navigation module 214 receives input from the tracking system 140 regarding the physical location and orientation of the surgical instrument 150 and an implant host. Tracking of the implant host may include tracking multiple individual bone structures, such as with tracking arrays 120. For example, during a total knee replacement procedure the tracking system 140 may individually track the femur and the tibia using tracking devices anchored to the individual bones (as illustrated in FIG. 1).

In an example, the control module 216 can process information provided by the navigation module 214 to generate control signals for controlling the surgical instrument 150. In certain examples, the control module 216 can also work with the navigation module 214 to produce visual animations to assist the surgeon during an operative procedure. Visual animations can be displayed via a display device, such as display device 130. In an example, the visual animations can include real-time 3-D representations of the implant, the implant host, and the surgical instrument 150, among other things. In certain examples, the visual animations are color-coded to further assist the surgeon with positioning and orientation of the implant.

In an example, the communication interface 218 facilitates communication between the control system 210 and external systems and devices. The communication interface 218 can include both wired and wireless communication interfaces, such as Ethernet, IEEE 802.11 wireless, or Bluetooth, among others. As illustrated in FIG. 1, in this example, the primary external systems connected via the communication interface 218 include the tracking system 140 and the surgical instrument 150. Although not shown, the database 230 and the display device 130, among other devices, can also be connected to the control system 210 via the communication interface 218. In an example, the communication interface 218 communicates over an internal bus to other modules and hardware systems within the control system 210.

In an example, the tracking system 140 provides location and orientation information for surgical devices and parts of an implant host's anatomy to assist in navigation and control of semi-active robotic surgical devices. The tracking system 140 can include a tracker (e.g., tracking array 120) that includes or otherwise provides tracking data based on at least three positions and at least three angles. The tracker can include one or more first tracking markers associated with the implant host, and one or more second markers associated with the surgical device (e.g., surgical instrument 150). The markers or some of the markers can be one or more of infrared sources, Radio Frequency (RF) sources, ultrasound sources, and/or transmitters. The tracking system 140 can thus be an infrared tracking system, an optical tracking system, an ultrasound tracking system, an inertial tracking system, a wired system, and/or a RF tracking system. One illustrative tracking system can be the OPTOTRAK® 3-D motion and position measurement and tracking system described herein, although those of ordinary skill in the art will recognize that other tracking systems of other accuracies and/or resolutions can be used.

U.S. Pat. No. 6,757,582, titled "Methods and Systems to Control a Shaping Tool," to Brisson et al., provides additional detail regarding the use of tracking systems, such as tracking system 140, within a surgical environment. U.S. Pat. No. 6,757,582 (the '582 patent) is hereby incorporated by reference in its entirely.

In an example, a surgeon can use the surgical instrument 150 to shape a target bone to accommodate a new prosthetic implant in place of an existing implant that failed. For example, as discussed above, it is not uncommon to need to revise a TKA by removing the prosthetic implants forming the artificial knee, reshape the femur and tibia, and implant new prosthetic implants to form a new artificial knee. In order to assist in performing a revision, the system 200 can track and control a surgical cutting instrument to perform precise cuts according to a virtual plan generated after removal of the old prosthetic (as discussed in additional detail below).

Figure 3:
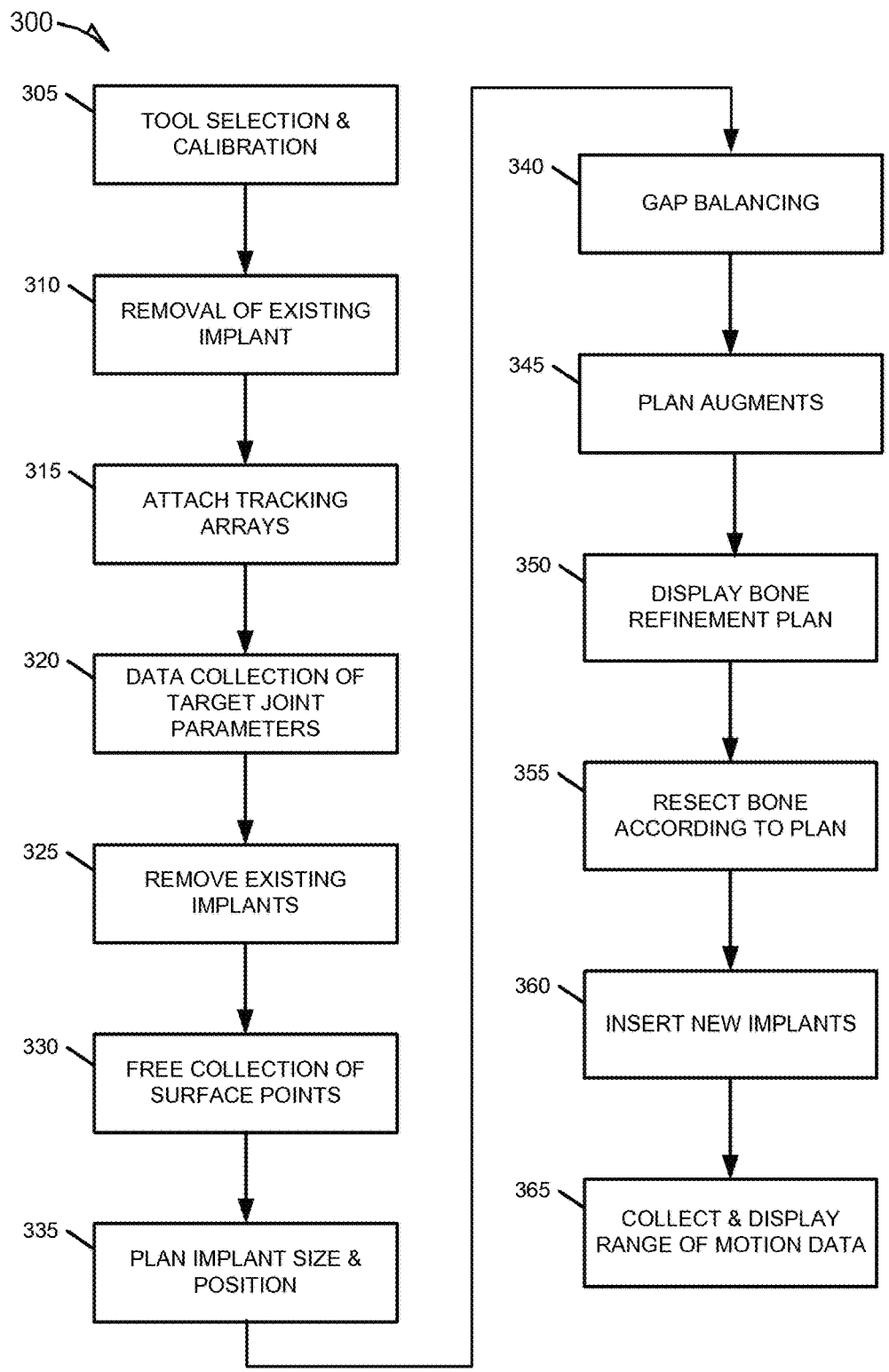
FIG. 3 is a flowchart illustrating a method for planning and performing image free implant revision surgery, according to an example embodiment.

Referring to FIG. 3, a method 300 for performing a revision surgical procedure using a robotic system, such as system 100 or 200, is provided. In this example, the method 300 includes operations such as tool selection and calibation at 305, removal of existing implant at 310, attaching tracking arrays at 315, collecting target joint data at 320, removing existing implants at 325, collecting surface points at 330, planning implant size and position at 335, balancing gap distances at 340, planning augments at 345, displaying bone refinement plan at 350, resecting bone(s) at 355, inserting new implants at 360, and collecting & displaying range of motion data at 365. The method 300 can be performed with more or few operations in certain examples. For example, in some example revision procedures joint or gap balancing at 340 can be an optional procedure.

According to step 305, the robotic system is connected and calibrated for the selected surgical tool and bur type. The tool is calibrated and validated for tracking during the surgical procedure. The overall surgical set-up 100 is illustrated in FIG. 1, with additional details provided in FIG. 2 discussing system 200, which in some examples is an extension of system 100.

As illustrated in step 310, the initial incision 110 is made, allowing a surgeon to access and remove the existing implants. In embodiments, the implants are removed prior to installing any trackers, such as tracking arrays 120, because the surgeon often needs to use a hammer to facilitate their removal from the bone and this could loosen the trackers if they are installed prior to the initial loosening and removal process. After the existing implants are loosened and removed, the surgeon will also remove any deteriorated or diseased bone that was behind the implant. In certain examples, the implants are then reinserted, to the extent possible, to enable data collection for planning purposes. Alternative embodiments provide for tracker pins with detachable couplings so that the pins are first inserted at the appropriate places and the trackers are then removed from the pins when the implants are being removed. In either method, the tracking arrays 120 are then attached 315 (or re-attached as the case may be) to the femur and tibia to enable real-time location monitoring of these bones using an infrared or other optical "line-of-sight" camera, such as tracking system 140, which also monitors the real-time location of any tracked tool, such as surgical instrument 150, being used by the surgeon.

According to step 320, a number of checkpoint and reference location data points are collected (also referred to as landmarks and pre-defined parameters). The location of a point probe, which is used for collecting coordinate points on bone and implant surfaces, is verified as to the location of the tip in relation to the trackers. Checkpoints are established in the system on the femur and tibia bones, including malleoli, as pre-established stationary reference points touched with the tip of the point probe. At various points during the overall procedure, these points will be touched with the point probe again to ensure accuracy within the tracking system as a whole. Typically, the hip center is then calculated by rotating the tracked femur in a circle about the hip joint until sufficient data has been collected.

Next, the knee center is determined. Still referring to step 320, femur landmark points are collected by palpation of those that exist with the tip of the point probe. Such femur landmark points include, for example, the knee center, most anterior point, most distal point, most posterior point, and medial and lateral epicondyle points, to the extent that these points exist and are reliable. In alternative embodiments, statistical values can be used in the place of these actual points. Next, the femur rotational reference is determined. The joint line reference is then determined by femur and tibia landmarks. In some patients, the joint line reference will be difficult to determine and in some embodiments, the other knee could be used for landmarks.

Still within the context of step 320, tibia landmark points can be collected by palpation with the tip of the point probe, including the tibial knee center, and most medial and lateral points of the tibia. Additionally, the tibial rotational reference is determined. Next, range of motion data is collected including the maximum *varus* and valgus in joint extension and flexion for purposes of gap balancing.

At step 325, the existing implants are again removed (assuming the particular procedure being performed allowed for reinsertion at step 310) and, at step 330, a multitude of points are then collected on the remaining bone surfaces of the femur and tibia by brushing or scraping the entirety of the remaining bone with the tip of the point probe or the tip of a drill, for example. This so-called "free collection" is actually the tracing or "painting" of a large portion of the remaining bone and is used to create a three-dimensional model or surface map of the bone surfaces in the computerized planning system, such as control system 210. The created 3D model of the remaining bone is then used as the basis for planning the procedure and necessary implant sizes. Typically, the landmark points are used to create a starting volume (initial 3D model), which is then shaved down to represent the actual size of the remaining bone during this free collection step. In an alternative embodiment, an infrared pointer could be built in to the handpiece and the location of the infrared light on the bone could be recorded by the system and a 3D model of the existing bone could be created that way as well.

In certain examples, the system uses landmarks and other information collected at step 320 to create a volumetric (voxelized) model of the joint. The virtual 3D model is aligned with the actual bone structures via the tracking data, such as tracking arrays 120 and point probe tracking (surgical instrument 150) via tracking array 155. Subsequently, during the collection of surface data at step 330, the volumetric virtual 3D model is reshaped to conform with the actual surface of the target bone. This process of iteratively reshaping a 3D model generated from landmarks and other patient specific information results in a very accurate 3D model of the actual target bone that can be used throughout the planning process. Virtually reshaping the 3D model provides an end result faster and more accurately than intra-operative imaging and without the logistical difficulties involved in intra-operative CT or similar scanning technologies.

According to step 335, the size and position of femoral and tibial implants are then established on the model in the system 200. Optionally, balancing of the gap between the femur and tibia is then planned at step 340. As used herein, balancing the gap refers to making sure the ligaments and soft tissue are appropriately tensioned to assist with stability and proper range of motion of the knee post-procedure. In embodiments, balancing is accomplished by rotating the femoral component when the knee is in flexion. In extension, the knee is balanced by releasing or thinning out the ligaments, but if the ligaments are released, there will be a need to re-measure.

Once the ideal implant size and positions have been chosen, the system 200 can optionally provide cross sectional views for evaluation and the potential use of femoral or tibial prosthetic augments can be evaluated and planned at step 345. For example, if there is a gap between the existing bone and the back of an implant, such as when diseased bone behind the prior implant needs to be removed, an augment will be used to eliminate that gap and, as a consequence, the cut plan will be changed to accommodate the augment.

Femoral and tibial checkpoints are then verified to ensure cuts are made where intended. Finally, according to 350, the bone refinement plan, resulting from the previously mentioned planning steps, is displayed over the representation of the remaining bone created as a result of the free collection step. This information is then displayed to the surgeon on a monitor 130 in the operating room. Then, at step 355, bone resection is performed and at step 360, the implants are inserted once the bones have been fully prepared in accordance with the bone refinement plan.

Figure 4:
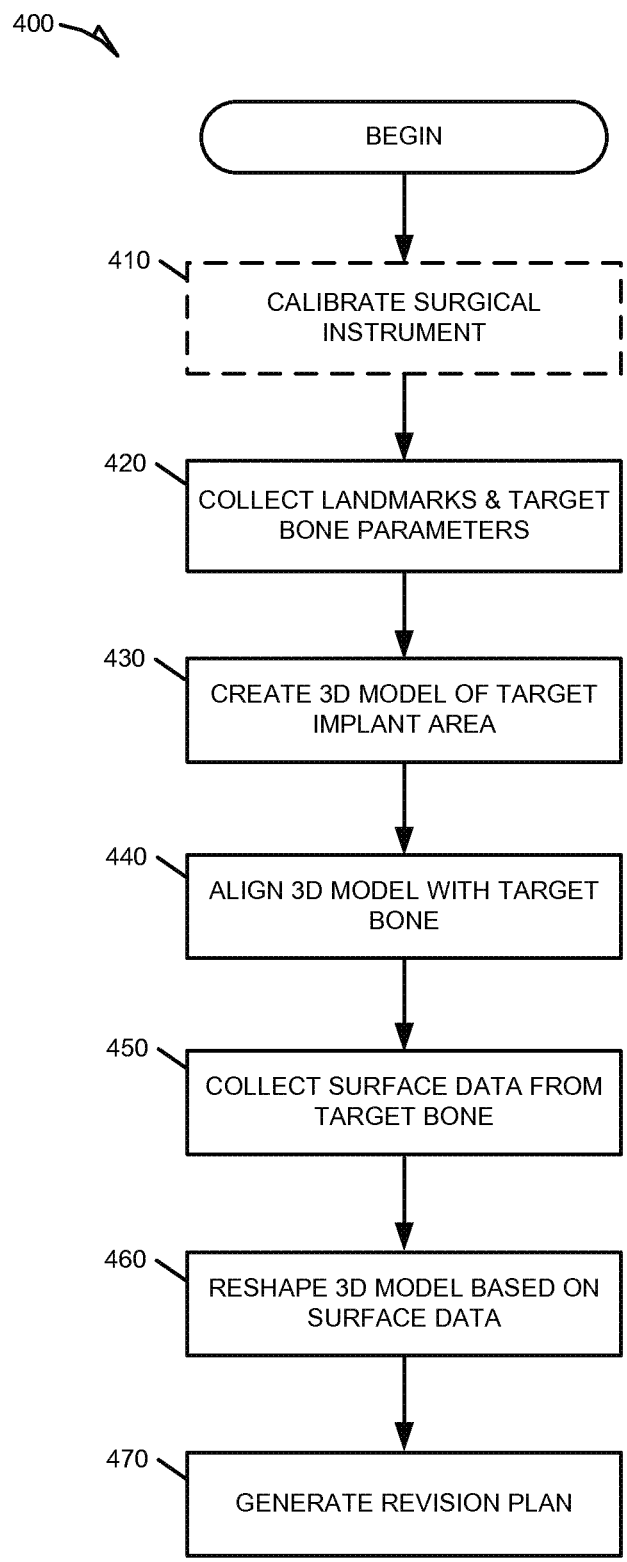
FIG. 4 is a flowchart illustrating a method for creating a virtual 3D model for resection of a target bone in a revision implant procedure, according to an example embodiment.

FIG. 4 is a flowchart illustrating a method 400 for creating a virtual 3D model for resection of a target bone in a revision implant procedure, according to an example embodiment. In this example, the method 400 includes operations such as point probe calibration at 410, collecting landmarks at 420, creating a 3D model at 430, optionally aligning the 3D model at 440, collecting surface data at 450, reshaping the 3D model at 460, and optionally generating a revision plat at 470. The method 400 is illustrated in FIG. 4 as including the various operations discussed above, in other examples the operations may be in a different order or a similar method may include fewer or more operations.

At 410, the method 400 can optionally begin with calibration of the surgical instrument 150. Calibration involves registering the working end of the surgical instrument 150 within the three dimensional coordinate system tracked by the tracking system, enabling the tracking system 140 to be able to accurately locate the surgical instrument 150. Calibration can be done by touching the working end of the surgical instrument, such as a point probe or cutting burr, to an object with known coordinates within the tracking system's coordinate space.

At 420, the method 400 continues with the control system 210 collecting landmarks and other pre-defined parameters of a target bone. In this example, the surgical instrument 150 can be used to touch the landmarks while the tracking system 140 sends location data to the control system 210. At 430, the method 400 continues with the control system 210, such as within the planning module 212, creating an initial 3D model of the target implant area of the target bone. In an example, the 3D model is a voxelized model of at least the portion of the target bone intended to receive a new implant. The 3D model can be generated from statistical bone models, using the landmarks and other pre-defined parameters to select size and shape from a database of statistical models. In other examples, the 3D model can be generated from pre-operative medical imaging scans, such as CT-scans. In some examples, the landmark and other pre-defined parameters are used to generate a rudimentary 3D model as a starting point without other inputs.

At 440, the method 400 continues with the control system 210 aligning the initial 3D model with the target bone. The method 400 continues at 450 with the control system 210 collecting surface data from the target bone. The surface data is received by the control system 210 from the tracking system 140 while the tracking system 140 monitors the location of the surgical instrument 150. The surface data can be collected using various attachments on the surgical instrument 150, such as a point probe attachment, a cutting burr, a burr guard, or a plate probe attachment, among others. Collection of the surface data is performed after the defective or worn-out prosthetic has been removed, and after any additional unwanted bone has been removed. In certain examples, the collection of surface points can be guided through display of an interactive animation (illustration) of the target bone surface, which can techniques to depict where on the target bone surface points still need to be collected. Color coding or similar techniques can be used to indicate past and needed point collection locations.

At 460, the method 400 continues with the control system 210 generating a reshaped 3D model based on the received surface data of the target bone. The reshaped 3D model becomes an accurate virtual representation of the actual surface contours of the target bone, which allows for accurate planning of revision implant size and position. Generation of the reshaped 3D model can be an iterative process, with the control system 210 updating the 3D model as the surface data is received from the tracking system 140. Iterative generation and display, such as on display device 130, of the reshaped 3D model allows the surgeon to judge how well the surface of the target bone has been captured during the planning portion of the revision procedure.

At 470, the method 400 can conclude with the control system 210 generating a revision plan based on the reshaped 3D model. The revision plan generation can include receiving implant selection and positioning inputs from a surgeon. In some examples, the system can suggest an initial implant size and location based on analysis of the reshaped 3D model. Once the implant size and location has been determined, the reshaped 3D model can be further analyzed to determine whether an augments need to be included to optimize fit of the revision implant. The voxelized 3D model allows for efficient display and virtual manipulation allowing the surgeon to quickly steps through layers of the 3D model to assess fit. Finally, the control system 210 can generate a cut or resection plan to reshape the target bone to best accommodate the revision implants and any selected augments.

In an embodiment, the present methods are utilized for the performance of revision procedures on total knee replacement patients, having multiple pre-existing prostheses including both femoral and tibial components.

While in accordance with the patent statutes the presently preferred and various alternative embodiments of the instant invention have been described in detail above, it should be understood that various other modifications and alternatives can be envisioned by those persons skilled in the art without departing from either the spirit of the invention or the scope of the appended claims.

Figure 5:
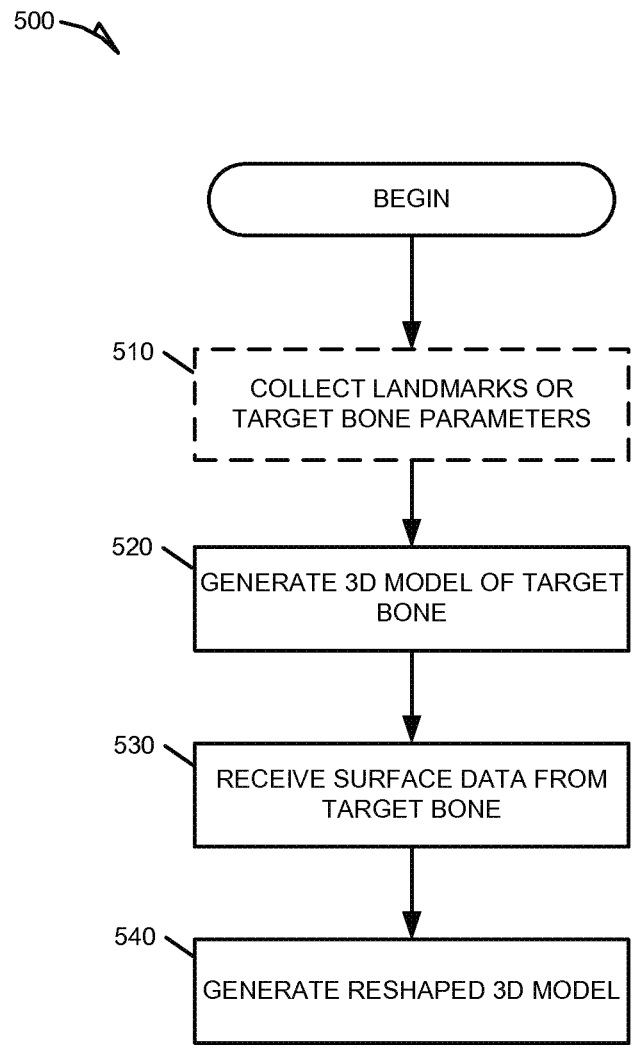
FIG. 5 is a flowchart illustrating a method for creating a 3D model for resection of a target bone in a revision implant procedure, according to an example embodiment.
Figure 6:
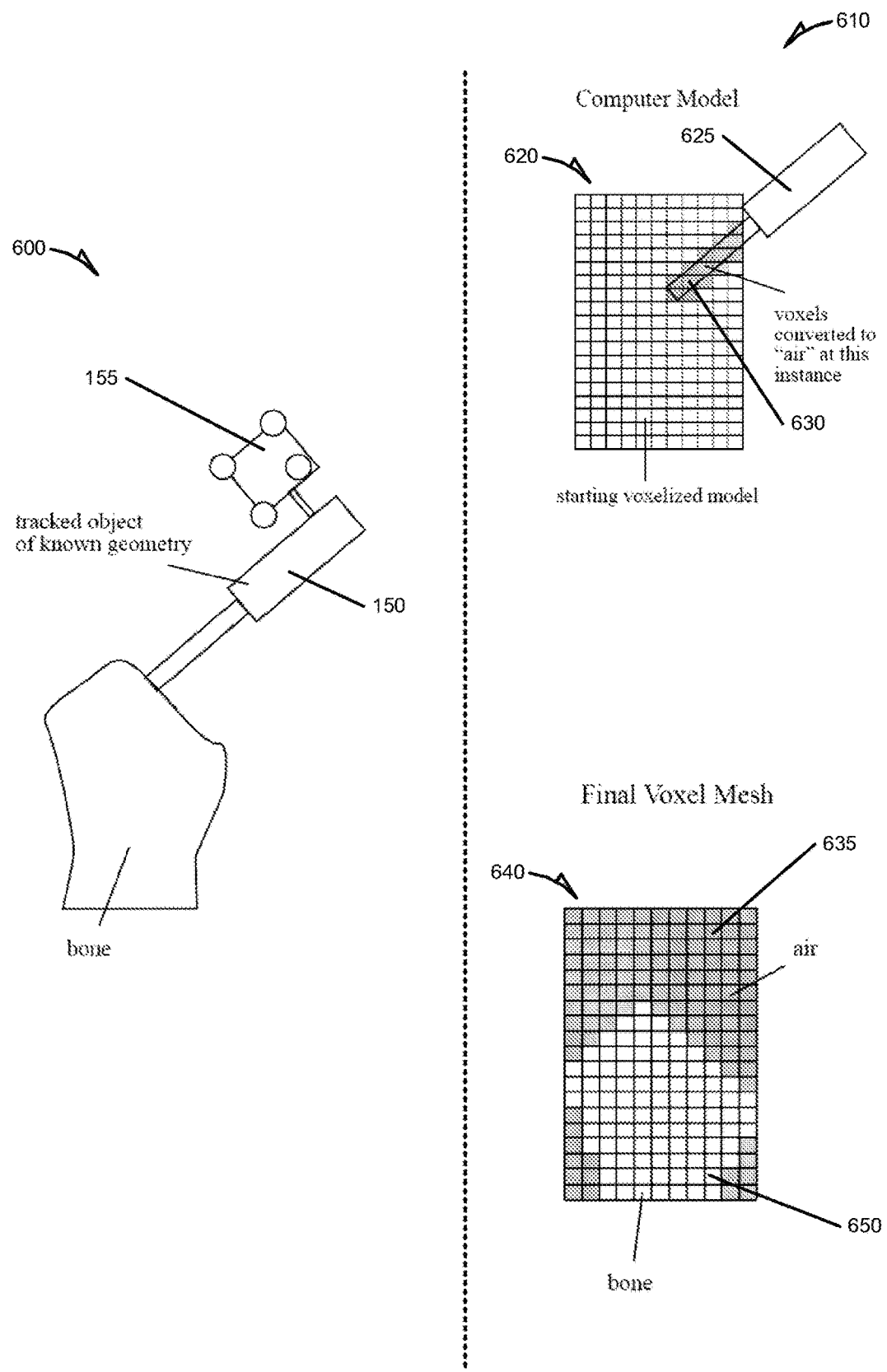
FIG. 6 is a diagram illustrating a method for creating a 3D model to be used in a revision procedure, according to an example embodiment.

FIG. 5 is a flowchart illustrating a method 500 for creating a 3D model for resection of a target bone in a revision implant procedure, according to an example embodiment. The method 500 illustrate an alternative to some of the operations discussed in reference to method 400. In this example, the method 500 includes operations such as optionally collecting landmarks or target bone parameters at 510, generating a 3D model of the target bone at 520, receiving suface data from the target bone at 530, and generating a reshaped 3D model at 540. In this example, the 3D model is a voxelized volume-base approximation of the target bone. Because of the reshaping approach the voxelized 3D model need only be a volume large enough to enclose the portion of the target bone that will be involved in the revision procedure. For example, the method 500 can begin with a cylinder or similar 3D polygon enclosing the distal end of a femur. FIG. 6 provides an additional illustration, in a 2-D manner, of the reshaping process discussed below.

At 510, the method 500 can optionally being with the control system 210 receiving data describing at least the basic dimensions of the target bone. In some examples, the control system 210 will receive landmarks and other size or shape parameters from a tracked surgical instrument contacting the target bone surface. At 520, the method 500 continues with the control system 210 generating an initial 3D model of the target bone. As discussed above, the initial 3D model can be as simple as a voxelized cylinder of sufficient size to enclose all relevant bone surfaces. For example, if the distal femur is the target bone area for the revision procedure, the voxelized cylinder can be sized sufficiently to enclose both condyles and a length of the femur proximal to the distal end longer than any envisioned implant. As illustrated in two dimensions in FIG. 6, the starting model 620 need only enclose the relevant bone surfaces (compare starting model 620 with reshaped model 640).

At 530, the method 500 can continue with the control system 210 performing volume subtraction on the initial 3D model based on surface data of the target bone received from a tracked surgical instrument, such as surgical instrument 150. As the surgical instrument 150 is moved over the surface of the target bone, position data from the tracking system 140 is used to reclassify voxels within the initial 3D model as boundary voxels or waste voxels, with waste voxels being removed. In some examples, boundary voxels may be smoothed or otherwise manipulated to generate a final reshaped 3D model. At 540, the method 500 concludes with the control system 210 generating a final reshaped 3D model. In some examples, the final reshaped 3D model is generated when the surgeon indicates that all surface points on the target bone have been captured. In other examples, the control system 210 determines from the received surface data input when the reshaped 3D model includes sufficient detail to generate a useable model. For example, the system can determine when it has a sufficient number of data points that form a contiguous surface or when interpolation between points drops below a pre-defined threshold.

FIG. 6 is a diagram illustrating a method for creating a 3D model to be used in a revision procedure, according to an example embodiment. FIG. 6 is divided into a physical world diagram 600 on the left and computer model diagrams 610 on the right. The physical world diagram 600 illustrates an example of surface mapping of the target bone with surgical instrument 150, which includes tracking array 155. The computer model diagrams 610 illustrate a volumetric subtraction method to transition from a starting model 620 to a reshaped model 640. In some examples, the control system 210 generates graphic user interface animations similar to the computer model diagrams 610. The starting model 620 is shown along with a surgical instrument model 625. The surgical instrument model 625 is illustrated changing voxels (depicted in 2 dimensions for clarity) to "air" or waste voxels 630, as the physical counter part (surgical instrument 150) collects surface data from the target bone. The reshaped model 640 is illustrated with waste voxels 635 (also noted as "air") and bone voxels 650.

Modules, Components and Logic

Certain embodiments of the computer systems, such as the control system 210 and the tracking system 140, described herein may include logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

Electronic Apparatus and System

Example embodiments may be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers. Certain example embodiments of a surgical instrument 150 can include a machine-readable medium storing executable instructions to be performed by the surgical instrument 150.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 7:
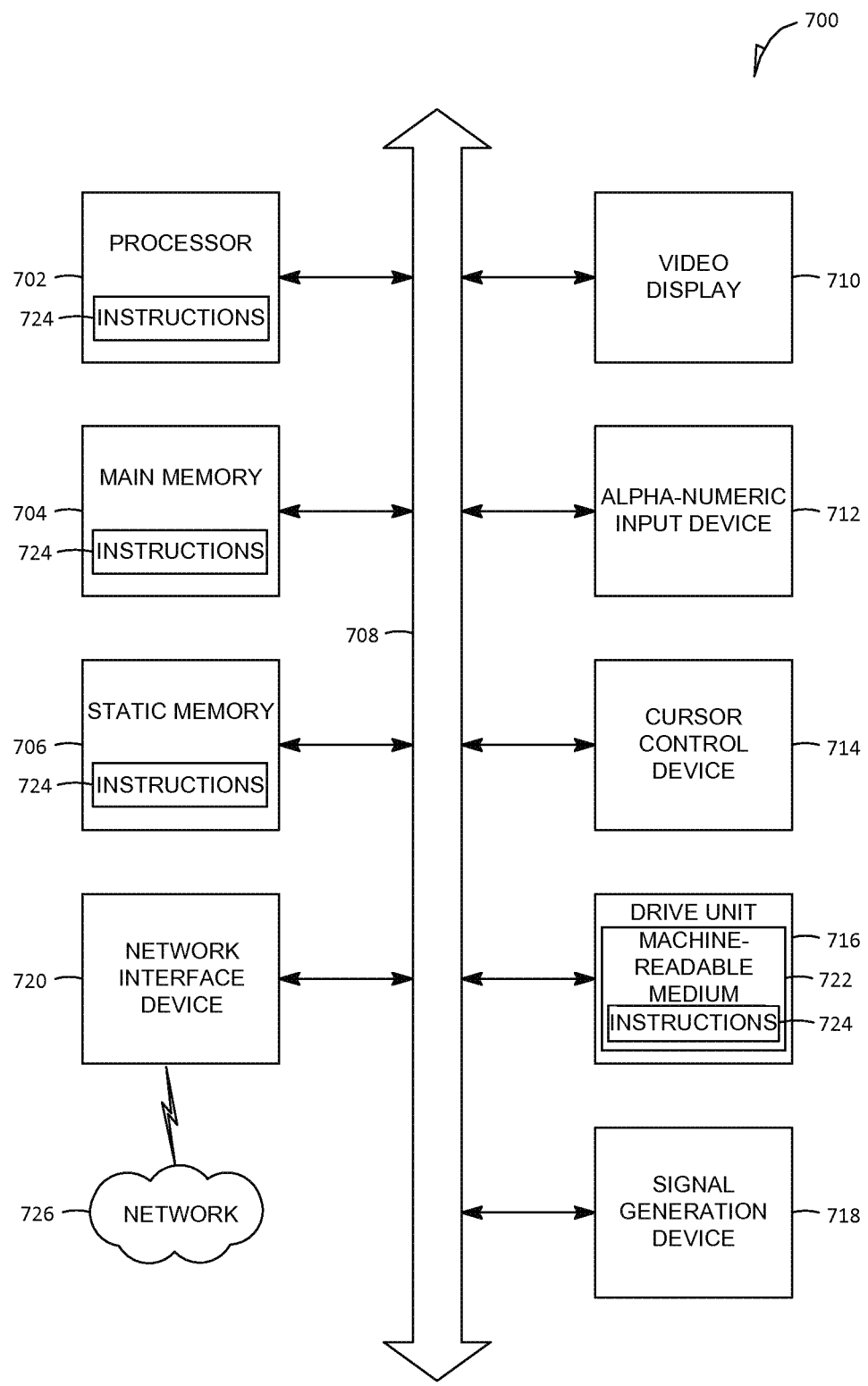
FIG. 7 is a diagrammatic representation of a machine in the example form of a computer system within which a set of instructions for causing the machine to perform any one or more of the methodologies discussed herein may be executed.

FIG. 7 is a block diagram of machine in the example form of a computer system 700 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 702 (e.g., a central processing unit (CPU), a graphics processing unit (GPU) or both), a main memory 704 and a static memory 706, which communicate with each other via a bus 708. The computer system 700 may further include a video display unit 710 (e.g., a liquid crystal display (LCD) or a cathode ray tube (CRT)). The computer system 700 also includes an alphanumeric input device 712 (e.g., a keyboard), a user interface (UI) navigation device (or cursor control device) 714 (e.g., a mouse), a disk drive unit 716, a signal generation device 718 (e.g., a speaker) and a network interface device 720.

Machine-Readable Medium

The disk drive unit (storage device) 716 includes a machine-readable medium 722 on which is stored one or more sets of instructions and data structures (e.g., software) 724 embodying or used by any one or more of the methodologies or functions described herein. The instructions 724 may also reside, completely or at least partially, within the main memory 704, static memory 706, and/or within the processor 702 during execution thereof by the computer system 700, the main memory 704 and the processor 702 also constituting machine-readable media or storage devices.

While the machine-readable medium 722 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices. Machine-readable storage device or computer-readable storage device should be construed as being a non-transitory physical device, such as a hard-drive or physical computer memory, but may also be similarly construed if denoted as a non-transitory computer-readable storage device.

Transmission Medium

The instructions 724 may further be transmitted or received over a communications network 726 using a transmission medium. The instructions 724 may be transmitted using the network interface device 720 and any one of a number of well-known transfer protocols (e.g., HTTP). Examples of communication networks include a LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Thus, methods and systems for navigation and control of an implant positioning device have been described. Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or examples have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim. Moreover, in the following claims, the terms "first," "second," "third," and so forth are used merely as labels, and are not intended to impose numerical requirements on their objects.

The Abstract of the Disclosure is provided to provide a quick overview of the subject matter of the present disclosure, not to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim.

The claimed invention includes:

1. A method of revising a total knee arthroplasty, the method comprising:
    preparing, using a portion of a surgical instrument, a virtual three-dimensional model of an existing implant within a target bone, wherein the surgical instrument comprises a point probe, a first tracking array, and a cutting burr;
    removing the existing implant from the target bone;
    installing a second tracking array on a portion of the target bone;
    preparing, using the point probe, a virtual three-dimensional model of the target bone following removal of the existing implant;
    removing an unwanted portion of the target bone;
    preparing, using the point probe, a virtual three-dimensional model of the target bone following removal of the unwanted portion;
    generating a surgical plan using a surgical system, wherein the surgical plan comprises:
        removing, using the cutting burr of the surgical instrument, a portion of the target bone according to a bone refinement plan, and
        selecting and planning a fit of a revision implant and, optionally, at least one augment, and
        wherein the surgical plan is based on at least one of the virtual three-dimensional model of the existing implant within the target bone, the virtual three-dimensional model of the target bone following removal of the existing implant, and the virtual three-dimensional model of the target bone following removal of the unwanted portion;
    tracking a three-dimensional location and an orientation of each of the surgical instrument, the target bone, and the revision implant using a surgical navigation system; and
    implanting the revision implant and, optionally, the at least one augment, according to the surgical plan.

2. The method of claim 1, further comprising tracking alignment of:
    (i) the target bone; and
    (ii) at least one of: the virtual three-dimensional model of the existing implant within the target bone, the virtual three-dimensional model of the target bone following removal of the existing implant, and the virtual three-dimensional model of the target bone following removal of the unwanted portion using the surgical navigation system.

3. The method of claim 1, wherein the at least one augment is selected from the group consisting of a femoral prosthetic augment, a tibial prosthetic augment, and a combination thereof.

4. The method of claim 1, wherein the target bone is selected from the group consisting of a femur, a tibia, and a combination thereof.

5. The method of claim 1, wherein the target bone comprises a femur and a tibia, and wherein the surgical plan further comprises balancing a gap between the femur and the tibia.

6. The method of claim 1, wherein:
the target bone comprises a femur and a tibia;
the surgical plan further comprises determining a joint line reference; and
tracking the three-dimensional location and the orientation of the target bone includes tracking the joint line reference.

7. The method of claim 1, further comprising collecting range-of-motion data and displaying the range-of-motion data virtually.

8. A system for revising a total knee arthroplasty, the system comprising:
a tracking system comprising a tracking sensor;
a surgical instrument comprising a cutting burr and a tracking array, wherein the tracking system is configured to monitor a current three-dimensional surgical instrument position and a current three-dimensional target bone position;
a control system comprising a communication interface and at least one processor coupled to a memory device, wherein the control system is coupled to the tracking system and is configured to receive tracking information identifying the current three-dimensional surgical instrument position and the current three-dimensional target bone position; and
a revision total knee implant and, optionally, at least one augment.

9. The system of claim 8, wherein the memory device includes instructions that, when executed by the at least one processor, cause the control system to perform an operation selected from the group consisting of collecting at least one pre-defined parameter, generating a virtual three-dimensional model, collecting a plurality of surface points, generating a reshaped virtual three-dimensional model, generating a virtual revision plan for preparing a target bone for implantation of a revision implant, and combinations thereof.

10. The system of claim 9, wherein the at least one pre-defined parameter characterizes an aspect of the target bone.

11. The system of claim 10, wherein generating the three-dimensional model comprises using the at least one pre-defined parameter to model a shape of at least a portion of the target bone.

12. The system of claim 9, wherein generating the reshaped three-dimensional model comprises:
collecting the plurality of surface points over a portion of the target bone surface associated with an implant revision procedure; and
generating the reshaped three-dimensional model based on the three-dimensional model and the plurality of surface points.

13. The system of claim 8, wherein the memory device includes instructions that, when executed by the at least one processor, cause the control system to use at least one pre-defined parameter to align a three-dimensional model of a target bone within a working coordinate system.

14. The system of claim 8, wherein the surgical instrument further comprises at least one of a burr guard, a plate probe attachment, and a point probe.

15. The system of claim 9, wherein the target bone is selected from the group consisting of a femur, a tibia, and a combination thereof.

16. The system of claim 8, wherein the at least one augment is selected from the group consisting of a femoral prosthetic augment, a tibial prosthetic augment, and a combination thereof.

17. The system of claim 8, wherein the tracking system is an optical tracking system.

\* \* \* \* \*